US009138349B2

(12) United States Patent
Wölfel et al.

(10) Patent No.: US 9,138,349 B2
(45) Date of Patent: Sep. 22, 2015

(54) LASER DEVICE, IN PARTICULAR, FOR OPHTHALMOLOGICAL LASER SURGERY

(75) Inventors: Mathias Wölfel, Erlangen (DE); Olaf Kittelmann, Berlin (DE); Daniel Thürmer, Nürnberg (DE)

(73) Assignee: Wavelight GmbH (DE)

( * ) Notice: Subject to any disclaimer, the term of this patent is extended or adjusted under 35 U.S.C. 154(b) by 202 days.

(21) Appl. No.: 12/965,307

(22) Filed: Dec. 10, 2010

(65) Prior Publication Data

US 2012/0150156 A1 Jun. 14, 2012

(51) Int. Cl.
*A61B 18/20* (2006.01)
*A61F 9/008* (2006.01)

(52) U.S. Cl.
CPC ....... *A61F 9/008* (2013.01); *A61F 2009/00897* (2013.01)

(58) Field of Classification Search
CPC ............ A61F 2009/00825; A61F 2009/00855; A61F 2009/00872; A61F 2009/00897; A61F 2009/00848; A61F 2009/00836; A61F 2009/0087; A61F 9/008; A61F 9/009; A61F 9/00831; G01J 1/4257; B23K 26/023; B23K 26/42; B23K 26/421; H01S 3/0014; H01S 3/0092
USPC .............................. 606/11, 4–6, 10; 600/558; 351/205–212; 356/121–127, 399–401, 356/604
See application file for complete search history.

(56) References Cited

U.S. PATENT DOCUMENTS

| | | | |
|---|---|---|---|
| 5,520,679 A * | 5/1996 | Lin .................................... | 606/5 |
| 5,941,874 A | 8/1999 | Hohla | |
| 7,027,233 B2 * | 4/2006 | Goldstein et al. ............. | 359/697 |
| 8,382,781 B2 | 2/2013 | Jeglorz et al. | |
| 8,430,869 B2 | 4/2013 | Wolfel et al. | |
| 2002/0097378 A1 | 7/2002 | Saito et al. | |
| 2002/0193704 A1 * | 12/2002 | Goldstein et al. ............. | 600/558 |
| 2005/0165386 A1 * | 7/2005 | Kurtz et al. ........................ | 606/4 |
| 2005/0197655 A1 * | 9/2005 | Telfair et al. ....................... | 606/5 |
| 2007/0010804 A1 * | 1/2007 | Rathjen et al. ..................... | 606/5 |
| 2007/0173794 A1 | 7/2007 | Frey et al. | |
| 2008/0078752 A1 * | 4/2008 | Bischoff et al. ........... | 219/121.72 |
| 2009/0118718 A1 * | 5/2009 | Raksi et al. ........................ | 606/5 |
| 2009/0171329 A1 * | 7/2009 | Raksi et al. ....................... | 606/11 |
| 2010/0305553 A1 * | 12/2010 | Kittelmann et al. .............. | 606/4 |

* cited by examiner

*Primary Examiner* — Gary Jackson
*Assistant Examiner* — Boniface N Nganga

(57) ABSTRACT

A laser device, in particular for ophthalmological laser surgery, comprising a laser source (14) for providing laser radiation, controllable scan components (20) for setting a focus position of the laser radiation, measuring components (30) for registering information that is representative of an actual position of the radiation focus, and also a control arrangement (22) controlling the laser source and the scan components. In accordance with the invention, the control arrangement has been set up to bring about the implementation of a test-mode operation of at least some of the scan components with the laser source turned off, in accordance with a predetermined test scan pattern, the test scan pattern defining at least one scan path for the radiation focus, and the control arrangement having been set up to bring about, during a scan movement along the scan path, repeatedly in succession a registration of the actual focus position without stopping the scan movement, and to ascertain a desired focus position, assigned to each registered actual focus position.

11 Claims, 2 Drawing Sheets

LASER DEVICE, IN PARTICULAR, FOR OPHTHALMOLOGICAL LASER SURGERY

TECHNICAL FIELD

The present invention relates to laser devices and, more particularly, to the testing of a scan function of a laser device.

BACKGROUND

Laser devices that operate with focused laser radiation in order to machine inorganic or organic material (e.g., human eye tissue) frequently exhibit controllable components that enable a scan function. With the scan function the radiation focus can be set precisely to differing positions in a plane orthogonal to the direction of propagation of the radiation (transverse scanning) or/and to differing positions along the direction of propagation of the radiation (longitudinal scanning). Examples of components that can serve for the scanning of laser radiation are swivel-mounted mirrors, deformable mirrors, electro-optical crystals, displaceably arranged lenses, lenses of variable refractive power, etc. Whenever scan components are mentioned within the scope of this disclosure, not only the optical components acting on the laser radiation are meant thereby, but rather also the totality of the components that are needed for scanning the laser radiation and that are capable of being influenced by electrical control signals of an electronic control arrangement. Accordingly, the scan components in the sense of the invention also include, in particular, the actuators that, where appropriate, are necessary for actuating the optical scan components and that are capable of being driven by the control signals of the control arrangement. Such actuators may, for example, include galvanometer drives, piezoelectric drives, motorized drives, controllable voltage-sources or current-sources, etc. It will be understood that the above enumeration of possible optical scan components and actuators is purely exemplary and is not to be understood as being restrictive.

SUMMARY

The embodiments of the present invention provide a laser device that may be intended and set up for ophthalmological laser surgery, comprising a laser source for providing laser radiation, controllable scan components for setting a focus position of the laser radiation, measuring components for registering information that is representative of an actual position of the radiation focus, and also a control arrangement controlling the laser source and the scan components, which has been set up to bring about the implementation of a test-mode operation of at least some of the scan components with the laser source turned off, in accordance with a predetermined test scan pattern, the test scan pattern defining at least one scan path for the radiation focus, and the control arrangement having been set up to bring about, during a scan movement along the scan path, repeatedly in succession a registration of the actual focus position without stopping the scan movement, and to ascertain a desired focus position assigned to each registered actual focus position. The test-mode operation is, as it were, a dry run in which the scan function of the laser device can be examined without laser radiation being given off by the laser device at the same time.

Ageing phenomena, a relative long period of disuse or/and data-transmission errors may have the result that a desired setting of the scan components of a laser device ordered by the control arrangement (corresponding to a particular desired position of the radiation focus) is not realized precisely and the actual setting of the scan components that is in fact achieved differs from the desired setting. With the laser source turned on, the actual position of the radiation focus would then differ from the desired position. In the case of the machining of dead or inorganic matter this may be acceptable, insofar as the machining can be repeated with a new workpiece if it turns out that the first machining was not sufficiently precise. In the case of living tissue—such as human eye tissue, for example—such a manner of proceeding is not feasible, for comprehensible reasons. The implementation of a prior test-mode operation of the scan components can provide certainty that in the course of the subsequent laser machining the desired value and the actual value are in fact sufficiently exactly close together, or/and it can provide elucidation about the extent of any possible deviations between desired and actual values, so that prior to the laser machining suitable corrective measures (e.g. exchange of at least some of the scan components, ascertainment of correction factors and adaptation of the desired values on the basis of the correction factors) can still be instigated.

The scan path defines a particular line of motion, along which the radiation focus is moved continuously during the scan movement, in which connection the reference to the radiation focus serves only for mental clarification, since in the test-mode operation no laser radiation impinges on the scan components and, accordingly, also no radiation focus is present. With the laser source switched on, the radiation focus that is then present would, of course, follow the line of motion predetermined by the scan path.

The control arrangement of the embodiments of the present invention can be set up to bring about a registration of the actual focus position in accordance with a given scan rate at regular temporal intervals. The temporal rate at which the actual focus positions are registered (scan rate) may be predetermined to be invariable, or it may be capable of being chosen by the user. For a given path velocity at which the (imaginary) radiation focus moves along the scan path, the control arrangement can ascertain the associated desired focus position on the basis of the given course of the path, the path velocity and the scan rate at each measured actual focus position.

Typically, the region within which the radiation focus can be adjusted is limited by constructional, physical or/and control-engineering presets. In this way, the user has a predetermined maximal scan field available which defines the outer boundaries for the scan movements of the radiation focus. In embodiments that enable solely transverse focus movements, the available scan field is accordingly a transverse surface. On the other hand, in embodiments that enable transverse and longitudinal focus movements, the available scan field is a three-dimensional space. Transversely the available scan field may have, for example, a circular outer boundary. In the three-dimensional case the available scan field may, for example, have circular cylindrical shape.

At least in some applications it may be the case that the available scan field is to be utilized for an application right up to its boundaries. Not only then, but particularly then, it is important to have certainty that also in the marginal regions of the available scan field the scan components are operating precisely and desired/actual deviations of the focus position only arise, if at all, within tolerable limits. Therefore, in embodiments of this invention the test scan pattern can define at least one scan path for the radiation focus which runs, at least at one point, along the boundary of a given maximal scan field. The scan path may, for example, touch the scan-field boundary once or several times in punctual manner or/and it may run along the boundary at least along a part of its path-length (where appropriate, even over its entire length).

The test scan pattern may define at least one circular scan path for the radiation focus running in a transverse plane orthogonal to the direction of propagation of the radiation. In the case of longitudinal scan capability of the scan components, the test scan pattern may even define several circular scan paths which run in various transverse planes, i.e. in transverse planes that are spaced from one another longitudinally. In this connection, for example, a first circular scan path may lie in a first transverse plane that delimits the available scan field on a first longitudinal side. A second circular scan path may lie in a second transverse plane that delimits the available scan field on the opposite longitudinal side. If the test scan pattern defines one or more further circular scan paths, these further circular scan paths may lie in transverse intermediate planes that lie between the two terminal transverse planes of the first and second circular scan paths.

Alternatively or additionally to one or more circular scan paths, the test scan pattern may define at least one helical path for the radiation focus, with a helix axis running along the direction of propagation of the radiation, or/and the test scan pattern may define at least one scan path running in meandering manner in a transverse plane orthogonal to the direction of propagation of the radiation. Such a meandering scan path may, for example, be bounded by an imaginary circle which it abuts at several points. The abutting of the meandering scan path against the imaginary boundary circle may be at least partially punctual; it may also be linear, in which case the meandering scan path then follows the boundary circle over a part of its path-length.

In a preferred configuration the meandering scan path exhibits a plurality of straight path portions running parallel to one another with mutual spacing, which are connected to one another alternately at opposite ends, in each instance in pairs. In this manner it is possible to examine the available scan field extensively for desired/actual deviations not only in the region of its margins but also in its interior.

In order to obtain a measure of the positioning precision of the scan components, the control arrangement may be set up to ascertain deviations between the desired focus positions and the actual focus positions and to compare the ascertained deviations with at least one predetermined deviation threshold. A certain number of positioning errors (i.e. cases in which the desired/actual deviation exceeds an assigned deviation threshold) may be tolerable. In one embodiment the control arrangement can therefore be set up to bring about, upon attaining a predetermined number of deviations exceeding the deviation threshold, the output of a visually or/and acoustically perceptible warning message. Further, in addition to the warning message, the control arrangement can also be configured to enter a disabling mode which prohibits an actuation of the laser device with the laser source turned on. The disabling mode can be, for example, configured in such a way that the control arrangement can exit it only after successful implementation of a further test-mode operation of the scan components.

Expressed more generally, the control arrangement of the embodiments of the present invention can be set up to disable, in the case of an unsuccessful implementation of the test-mode operation, operation of the laser device with the laser source turned on.

The implementation of a test-mode operation of the scan components may be sensible, in particular, after a relatively long down-time of the laser device, during which it was out of service. Therefore, it is desirable in some embodiments of the present invention to set up the control arrangement to bring about at start-up of the laser device the implementation of the test-mode operation in program-controlled manner for the purpose of establishing the operational readiness of said laser device. It will be understood that other triggering events that bring about the implementation of the test-mode operation may have been defined.

BRIEF DESCRIPTION OF THE DRAWINGS

The invention will be elucidated in more detail below on the basis of the appended drawings. Represented are.

DETAILED DESCRIPTION

Figure 1:
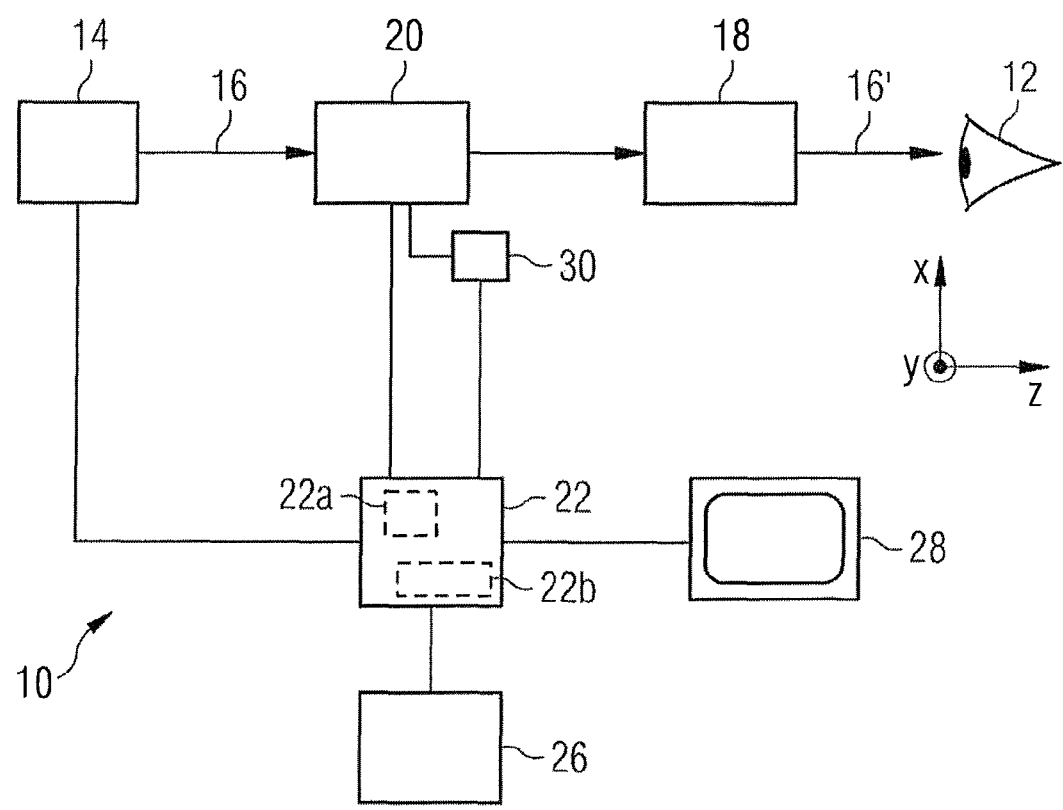
FIG. 1: in schematic block representation, elements of a laser device according to an exemplary embodiment.

The laser device shown in FIG. 1—denoted therein generally by 10—serves for machining an object, shown in the exemplary case as a human eye 12, by means of ultra-short-pulse focused laser radiation. 'Ultra-short-pulse' here means pulse durations within the range from femtoseconds to at most single-digit picoseconds, which is exemplary as the embodiments of the present invention can be configured for use with any laser system having a laser scanning functionality. The effect utilized for the machining is the so-called laser-induced optical breakthrough, which results in a photo-disruption within the material being machined (here, eye tissue). By placing a plurality of such photodisruptions side by side, diverse incision figures can be generated in the eye 12 and, therein above all, in the cornea.

The laser device 10 includes a laser source 14, which can be a femtosecond laser source, which provides a laser beam 16 which after passing through an optical path-length, along which various elements for beam guidance and shaping are arranged, impinges on the eye 12 as a focused laser beam 16'. The aforementioned elements for beam guidance and shaping include focusing optics 18—constituted, for example, by an f-theta objective—as well as scan components 20 indicated here schematically by a single block. It is to be emphasized that the representation of the focusing optics 18 and of the scan components 20 in FIG. 1 as separate blocks serves solely for the purpose of better illustration. It is readily conceivable that some of the optical components responsible for the focusing of the laser beam 16 may also assume scan functionality. For instance, it is not ruled out that one or more lenses contained in the focusing optics 18 or even the focusing optics 18 as a whole is/are adjustable for the purpose of longitudinal positioning of the beam focus in the direction of beam propagation. Nevertheless, in a desirable configuration the optical components serving for the scanning of the laser beam 16 are separated from the optical components serving for focusing the laser beam 16 and are consequently arranged outside the focusing optics 18.

For example, the scan components for transverse scanning of the laser beam 16 may include a pair of rotatably arranged deflecting mirrors, the axes of rotation of which are perpendicular to one another, and also, assigned to each of the deflecting mirrors, an individually controllable galvanometer drive. Such galvanometrically actuated deflecting mirrors are known by those having skill in the art; there is therefore no need for any more detailed elucidation of them at this point. For the purpose of longitudinal scanning of the beam focus, the scan components may, for example, utilize a lens which is provided as part of beam-expanding optics (not represented in any detail), which for the purpose of varying the divergence of the laser beam 16 is adjustably arranged in the direction of beam propagation or is adjustable as regards its refractive power. An associated actuator in the form of a linear drive or in the form of a controllable voltage-source may then likewise be part of the scan components 20.

In a minimal format of the laser device 10 the scan components 20 are in any case designed for transverse scanning of the laser beam 16. In a more desirable configuration the scan components 20 can also be set up for longitudinal scanning. Incidentally, it will be understood that, in addition to the aforementioned exemplary configurations of the scan components, other principles of action may find application that enable a transverse or/and longitudinal scanning, for example a controlled beam deflection in an electro-optical crystal or an influencing of the divergence of the laser beam by deformation of an optical mirror arranged in the path of propagation of the laser beam 16.

The embodiments of the laser device 10 of the present invention can include, in addition, a processor-based control arrangement 22 for controlling the operation of the laser device. The control arrangement 22 is program-controlled; the control program of the control arrangement 22 is saved in a memory arrangement 26.

Even though the control arrangement 22 in FIG. 1 is represented by a single block, it will be understood that its control functions can be split up to various control modules which can be incorporated into different modules on separate controller boards. For instance, the control arrangement 22 may include a scan control module, drawn with dashed lines at 22*a*, which is responsible for the control of the scan components 20 and together with these—or together with at least some of the scan components 20—is structurally integrated into a scanner which has been preassembled as a separate component. The remaining control functions of the control arrangement 22 may, for example, be combined in a central control module 22*b* situated structurally outside this scanner, which is responsible, inter alia, for the synchronization of the operation of the laser source 14 and the operation of the scan components 20 and is able to send corresponding control commands to the scan control module 22*a* in order to start a scan procedure. The concrete adjusting operations for setting the scan components 20 can then be controlled by the scan control module 22*a* in accordance with suitable scan data which were previously loaded into the scan control module 22*a* and which define a scan pattern to be executed.

Corresponding to the possible splitting of the control arrangement 22 into separate control modules, the memory arrangement 26 can also be split up into separate memory modules, and the aforementioned control program may be been split up into separate program modules which, in turn, may be stored in various memory modules. For example, a memory module can be integrated, jointly with the scan control module 22*a*, into the aforementioned scanner and may store such program parts that are necessary for the control of the scan components 20. One or more further memory modules, on the other hand, can be assigned to the central control module 22*b* and may store the remaining program parts of the control program.

Connected furthermore to the control arrangement 22 is an output unit 28, here shown in the exemplary form of a monitor, on which test results yet to be elucidated can be output which are obtained within the scope of a test-mode operation of the laser device 10. Even though not represented in any detail in FIG. 1, alternatively or additionally to the monitor 28 a printer can be linked to the control arrangement 22, in order to output the aforementioned test results in printed form.

In FIG. 1 a triaxial coordinate frame has in addition been drawn in which, according to conventional notation, spans an x-y transverse plane orthogonal to the direction of propagation of the radiation of the laser beam 16, whereas the z-axis defines the longitudinal direction of beam propagation.

The control arrangement 22 of the embodiments of the present invention can be set up to implement, with the laser source 14 turned off, a test-mode operation in which the scan components 20 or at least some of the same are controlled in accordance with a predetermined test scan pattern. This dry run, in which no laser radiation is given off from the laser source 14, is intended to enable a positional check by which it is to be ensured that the entire region in which the beam focus in the x-, y- and, where appropriate, z-directions can be nominally set can actually be traversed. In particular, the positional check is to enable an examination of any possible desired/actual deviations of the focus position in the entire scan region. The maximal scan region, which in the present case—on the assumption of both transverse and longitudinal scan capability—is a three-dimensional space, is also designated here as the available scan field.

Measuring components (measuring device) 30 indicated schematically as a single block can be provided for the purpose of registering the actual setting condition of at least some of the scan components 20 metrologically and supplying corresponding measured values to the control arrangement 22. The latter is able to calculate values for the actual position of the beam focus from the measured values supplied. For example, for the purpose of registering the actual position of a rotatable deflecting mirror contained in the scan components 20 the measuring components 30 may include a position-detector as shown and described in European Patent EP 1 295 090 B1, which is hereby incorporated by reference in its entirety.

The calculated actual focus positions can be stored by the control arrangement 22 in the memory arrangement 26, assigned to associated desired focus positions. In the course of a machining of an eye 12, the desired focus positions are predetermined, for example in tabular form, by specification of the respective x-, y- and z-values. After conclusion of the machining of the eye 12, the control arrangement 22 can compare the actual values of the focus position, ascertained in the meantime, with the associated desired values and can output corresponding information via the monitor 28 or an attached printer. From this information an operating surgeon can appraise the quality of the machining and, ultimately, the success of the operation.

The aforementioned test-mode operation of the embodiments of the present invention is expedient, above all, when (but not only when) during the scan operation of the laser device 10 measured values for actual focus positions can indeed be recorded and stored by means of the measuring components, but the laser device 10 has not been set up to evaluate the actual focus positions during the scan operation with regard to deviations from the associated desired focus positions and, where appropriate, to intervene in corrective manner if the deviations are too great. Such circumstances may obtain, for example, if the desired and actual data of the focus positions cannot be transmitted from the scan control module 22a to the central control module 22b during a scan procedure, but rather the central control module 22b obtains access to these data only after conclusion of the scan procedure. In this way, the test-mode operation enables an advance inspection of the positioning quality of the scan components 20. Depending on the result of the test-mode operation, the operating surgeon or an evaluating program operating automatically is able to decide that the available scan field can be traversed with sufficient precision in order to implement a planned machining of an eye, or measures such as an exchange of at least some of the scan components may be necessary, should the traversable scan region prove to be insufficient.

The test-mode operation can be started automatically by the control arrangement 22 of the embodiments of the present invention; that is to say, without separate intervention on the part of a user, for example in the course of the system start upon switching on a master switch, not represented in any detail, of the laser device 10 or/and in a timed manner after expiration of predetermined time-intervals.

Figure 2:
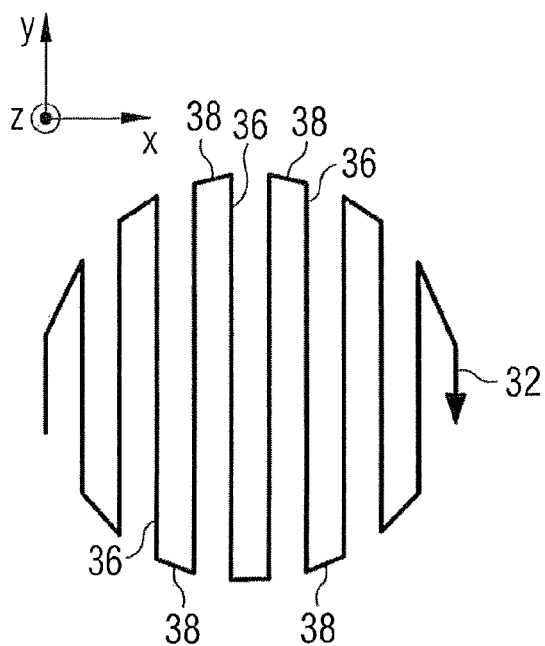
FIG. 2: an example of a meandering scan path as an integral part of a test scan pattern capable of being realized by the laser device shown in FIG. 1 in a test-mode operation.
Figure 3:
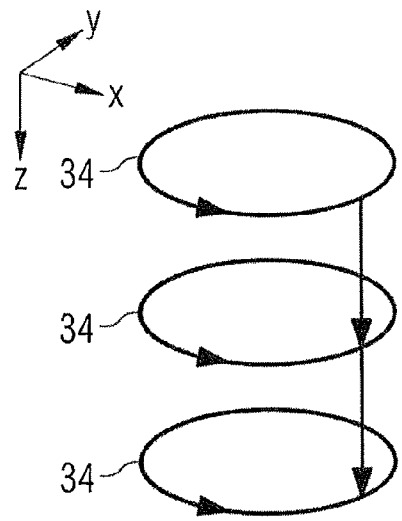
FIG. 3: an arrangement of several longitudinally spaced transverse circular scan paths as an integral part of a test scan pattern in accordance with the teachings of the present invention.
Figure 4:
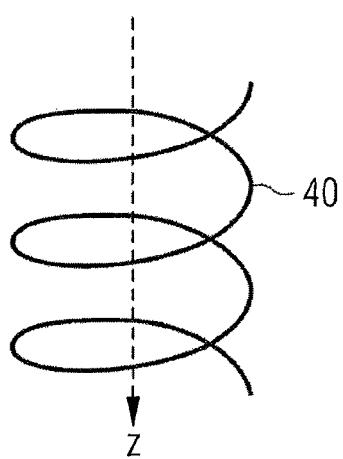
FIG. 4: an example of a helical scan path as an integral part of a test scan pattern in accordance with the teachings of this invention.

For an explanation of a test scan pattern that can be executed within the scope of the test-mode operation of the embodiments of the present invention, reference will now additionally be made to FIGS. 2 to 4. On the assumption of a circular cylindrical available scan field (i.e. a scan field, the transverse outer boundary of which is circular), the test scan pattern may, for example, include a meandering scan path 32 to be swept in a given transverse plane or/and several (in the exemplary case shown, three) circular scan paths 34 to be swept in various transverse planes. The meandering scan path 32 shown in FIG. 2 extends within the boundaries of an imaginary circumscribed circle (not represented in any detail) which marks the transverse outer boundary of the available scan field. Within this circumscribed circle the meandering scan path 32 is configured in the manner of a serpentine pattern with a plurality of straight path portions 36 running side by side in parallel with a spacing, the path portions 36 being connected to one another alternately at opposite ends by connecting path portions 38. As soon as one of the straight path portions 36 impinges on the imaginary circumscribed circle, a connecting path portion 38 joins on which corresponds either to the circular-arc shape of the imaginary circumscribed circle or—as represented in FIG. 2—to a chord of the circumscribed circle. With such a meandering scan path 32 the scan region that is available in the transverse direction can be inspected in a detailed manner both at the region boundaries and in the interior. Depending on the desired density of the inspection points, the mutual spacing of the straight path portions 36 can be chosen to be closer or more distant.

The circular scan paths 34 shown in FIG. 3 serve, above all, for inspection of the scan precision over the longitudinal extent (z-length) of the available scan field. In this connection the circular scan paths 34 may be dimensioned in such a way that they correspond to the transverse outer boundary of the available scan field. Smaller diameters for the circular scan paths 34 can also be selected, so that they run radially within the transverse outer boundary of the available scan field.

In the longitudinal direction it is desirable that the two outermost circular scan paths—in the view shown in FIG. 3 accordingly the uppermost and lowest circular scan paths—are situated on the longitudinal region boundaries of the scan field. The middle one of the circular scan paths 34 shown in FIG. 3 may, for example, lie in the longitudinal centre of the available scan field.

The temporal sequence in which the meandering scan path 32 and the circular scan paths 34 are swept can in itself be chosen arbitrarily. For example, firstly the meandering scan path 32 can be swept, and subsequently the three circular scan paths 34. The reverse sequence is equally conceivable. Also, firstly a fractional number of the circular scan paths 34 can be swept, then the meandering scan path 32 can be interpolated before the remaining residual number of circular scan paths 34 are processed.

The transverse plane in which the meandering scan path 32 lies may correspond to the transverse plane of one of the circular scan paths 34. It may, alternatively, be executed in a transverse plane that is different from the circular scan paths 34. For a still more detailed functional check, the embodiments of the present invention can be configured to execute the meandering scan path 32 several times in various transverse planes.

A further exemplary test scan path which can be set in the test-mode operation in respect of the scan components 20 is shown in FIG. 4 in the form of a helical scan path 40. The helix axis of the helical scan path 40 preferentially runs parallel to the z-direction, that is to say, in the direction of propagation of the radiation. The helical scan path 40 can run along the outer boundaries of the available scan field. In the exemplary case that is shown, said helical scan path comprises three helical turns; it will, however, be understood that the helical scan path may be composed of a larger or smaller number of turns.

Within the scope of the invention the test scan paths shown in FIGS. 2 to 4 may be contained in the test scan pattern individually or in arbitrary combination.

The meandering scan path 32, the circular scan paths 34 and the helical scan path 40 are predetermined continuous paths, for the realization of which the scan components 20 are appropriately adjusted continuously. A timer control—implemented, for example, by the control program of the control arrangement 22—gives rise at regular temporal intervals to a registration of the actual setting condition of at least some of the scan components 20 by the measuring components 30 and hence to a registration of the actual focus position. This registration can be effected while the scan path in question is being swept continuously, that is to say, while the fraction of the scan components 20 needed for the sweeping of the scan path is being continuously adjusted. The scan components 20 accordingly are not required to be stopped before an actual focus position is registered. Since the test-mode operation is implemented without laser radiation, in the case of the actual focus position it is a question only of an imaginary position that corresponds to the actual setting condition of the scan components 20 but that, on account of the absence of a beam focus, is not reflected in a real focus position. The temporal scanning interval of the actual focus position may, for example, lie within the range from a few µs up to several ms (for example, about 10 ms). The number of scan values obtained during a test-mode operation (i.e. the number of actual focus positions ascertained) may, for example, amount to several hundred, several thousand or even still more. This comparatively large number of scan values enables a reliable statement about the correct scanner function in the entire available scan field.

For each registered actual focus position the control arrangement 22 of the embodiments of this invention can ascertain an associated desired focus position. Said control arrangement can ascertain this from the known path progression of the scan path being executed instantaneously (e.g. meandering scan path 32 or one of the circular scan paths 34), from the path velocity—that is to say, the speed of adjustment of the scan components 20—and also from the time-interval with which the actual focus position is scanned. The desired focus positions ascertained in this way are stored by the control arrangement 22 in the memory arrangement 26, assigned to the registered actual focus positions.

Attention should be drawn to the fact that, depending on the scan path, it may be sufficient to take into account for the desired focus positions or/and the actual focus positions only one or two coordinates instead of all three coordinates of the x-, y- and z-coordinate system. For example, for the meandering scan path 32 it may suffice to specify the desired focus positions or/and the actual focus positions only by means of the x- and y-coordinate values. As far as the circular scan paths 34 are concerned, for the desired focus positions and the actual focus positions it may suffice to register and store only the z-coordinate value and a transverse coordinate value, for example the x-coordinate value. To the extent that the laser device 10 enables this, it may, however, be desirable to register all three coordinate values for all the desired focus positions and actual focus positions.

After execution of the test scan pattern, the control arrangement 22 undertakes an analysis of the recorded desired focus positions and actual focus positions. In this connection it ascertains deviations between the desired focus positions and the actual focus positions and compares the deviations found with at least one predetermined threshold. For example, the control arrangement 22 may ascertain the deviations between the desired focus positions and the associated actual focus positions separately for each coordinate axis individually and compare them with an assigned deviation threshold. The deviation threshold to be applied may be the same for the coordinate axes or different for different coordinate axes. If desired, the control arrangement 22 may additionally ascertain an overall deviation from the deviations found along the individual coordinate axes, for instance in the manner of the Euclidean distance. It can also compare the overall deviation found in this way with an assigned deviation threshold. It will be understood that each deviation threshold may either be permanently predetermined or capable of being selected by a user via an input unit, not represented in any detail, connected to the control arrangement 22.

A part of the evaluation performed by the control arrangement 22 can be a plausibility check. Actual focus positions that differ excessively from their assigned desired focus position can be rejected by the control arrangement 22 as implausible and disregarded in the course of the further evaluation.

The control arrangement 22 can count those cases in which a desired/actual deviation exceeds an associated deviation threshold. If the number of cases exceeding a given deviation tolerance attains a certain predetermined limit, the control arrangement 22 can instigate the output of a warning on the monitor 28. The warning informs the user that the precision of the scan is not sufficient. As a further response to the reaching of the limit for the number of permissible errors, the control arrangement 22 can enter a disabling mode which prohibits operation of the laser device 10 with the laser source 14 turned on. After successful implementation of a further test-mode operation, in which the number of desired/actual deviations lying above the deviation threshold has remained below the permissible limit, the disabling mode can be cancelled and the operation of the laser device 10 enabled with the laser source 14 turned on.

Alternatively or additionally, the control arrangement 22 can be set up to evaluate the ascertained desired/actual deviations in no further detail and to output them, where appropriate together with the actual focus positions or/and the desired focus positions, on the monitor 28 or in some other form. In this case the assessment of the test result is left to the user.

The methodology disclosed hitherto permits an inspection and determination as to whether the dynamic behavior of the scan components 20 (generally, of the scan system) of a laser device corresponds to the specified requirements and whether the available scan space can be utilized, that is to say, traversed, in its totality. To this end, the test scan pattern of the embodiments of this invention can define one or more scan paths that are situated in such a manner in the available maximal scan space that as a result of sweeping these scan paths it can be ensured that the scan system can traverse the entire possible scan region cleanly and that problems associated with the described aspects of the operation of the scan system are reduced or eliminated. The sweeping of the scan paths can constitute a continuous movement, that is to say, the scan system would not stop at the scan points for the purpose of local settling. This temporally triggered position measurement with continuous scan movement may result in the appearance of tracking errors, which, however, can be accepted as a slightly diminished measuring accuracy, since despite such tracking errors the evidence of full usability of the available maximal scan space which is being striven for can be provided.

Although embodiments of the proposed system and technique of the present invention have been illustrated in the accompanying drawings and described in the description, it will be understood that the invention is not limited to the embodiments disclosed herein. In particular, the proposed technique is capable of numerous rearrangements, modifications and substitutions without departing from the scope of the invention as set forth and defined by the following claims.

The invention claimed is:

1. A laser device for ophthalmological laser surgery, comprising:
a laser source configured to provide laser radiation;
controllable scan components configured to set a focus position of the laser radiation;
measuring components configured to detect the position of a scan component to register information that indicates an actual position of the radiation focus;
a control arrangement configured to:
control the laser source and the scan components,
implement a test-mode operation of at least one of the scan components with the laser source turned off, in accordance with a predetermined test scan pattern that defines at least one scan path for the radiation focus,
initiate, during a scan movement along the scan path, repeatedly in succession and at regular temporal intervals a registration of the actual focus position without stopping the scan movement, and
ascertain a desired focus position, assigned to each registered actual focus position, from a progression of the scan path, a time-interval with which the actual focus position is registered, and a velocity of the scan path.

2. The laser device according to claim 1, wherein the control arrangement has been set up to bring about a registration of the actual focus position in accordance with a given scan rate at regular temporal intervals.

3. The laser device according to claim 1, the control arrangement further configured to implement the test-mode operation in accordance with a second test scan pattern defining at least one meandering scan path, the meandering scan path having a serpentine pattern with a plurality of straight path portions and a plurality of connecting path portions, the straight path portions running side by side in parallel with a spacing, the connecting path portions connecting the path portions to one another alternately at opposite ends, the serpentine patter defined in a transverse plane orthogonal to the direction of propagation of the radiation.

4. The laser device according to claim 3, wherein the meandering scan path is bounded by an imaginary circle that the meandering scan path abuts at the connecting path portions.

5. The laser device according to claim 1, wherein the control arrangement has been set up to ascertain deviations between the actual focus positions and associated desired focus positions and to compare the ascertained deviations with at least one predetermined deviation threshold.

6. The laser device according to claim 5, wherein the control arrangement has been set up to bring about, upon attaining a predetermined number of deviations exceeding the deviation threshold, the output of a visually or/and acoustically perceptible warning message.

7. The laser device according to claim 1, wherein in the case of an unsuccessful implementation of the test-mode operation the control arrangement has been set up to disable operation of the laser device with the laser source turned on.

8. The laser device according to claim 1, wherein the control arrangement has been set up to bring about, upon start-up of the laser device, the implementation of the test-mode operation in program-controlled manner for the purpose of establishing the operational readiness of said laser device.

9. The laser device according to claim 1, the at least one scan path being a helical path with a helix axis parallel to the direction of propagation of the radiation.

10. The laser device according to claim 1, wherein the test scan pattern defines at least one scan path for the radiation focus, which at least partially runs along the boundary of a given maximal scan field.

11. The laser device according to claim 1, wherein the test scan pattern defines a plurality of circular scan paths for the radiation focus, each circular scan path running in a different transverse plane orthogonal to the direction of propagation of the radiation.

* * * * *